(12) United States Patent
Meissner et al.

(10) Patent No.: US 11,464,743 B2
(45) Date of Patent: Oct. 11, 2022

(54) GATE FOR A TABLET DISCHARGE OF A TABLET PRESS AND METHOD FOR ACTUATING A GATE

(71) Applicant: Fette Compacting GmbH, Schwarzenbek (DE)

(72) Inventors: Friedrich Meissner, Schwarzenbek (DE); Stefan Luedemann, Hamburg (DE)

(73) Assignee: Fette Compacting GmbH, Schwarzenbek (DE)

(*) Notice: Subject to any disclaimer, the term of this patent is extended or adjusted under 35 U.S.C. 154(b) by 0 days.

(21) Appl. No.: 16/458,621

(22) Filed: Jul. 1, 2019

(65) Prior Publication Data
US 2020/0009057 A1  Jan. 9, 2020

(30) Foreign Application Priority Data

Jul. 4, 2018 (DE) .................. 102018116143.34

(51) Int. Cl.
| | | |
|---|---|---|
| *A61K 9/20* | (2006.01) | |
| *B30B 11/00* | (2006.01) | |
| *B30B 11/02* | (2006.01) | |
| *B30B 15/30* | (2006.01) | |
| *B30B 15/32* | (2006.01) | |

(52) U.S. Cl.
CPC ............. *A61K 9/20* (2013.01); *B30B 11/005* (2013.01); *B30B 11/02* (2013.01); *B30B 15/304* (2013.01); *B30B 15/32* (2013.01)

(58) Field of Classification Search
CPC ............................. B30B 11/005; B30B 15/32
See application file for complete search history.

(56) References Cited

U.S. PATENT DOCUMENTS

| | | | | |
|---|---|---|---|---|
| 4,066,173 A | * | 1/1978 | Adams ................ | B30B 11/005 377/6 |
| 4,570,229 A | * | 2/1986 | Breen ................... | B30B 11/005 264/40.1 |
| 4,643,291 A | | 2/1987 | Counter et al. | |

FOREIGN PATENT DOCUMENTS

| | | |
|---|---|---|
| CN | 205112500 U | 3/2016 |
| CN | 106553373 A | 5/2017 |
| EP | 1974895 A2 | 10/2008 |

(Continued)

OTHER PUBLICATIONS

EP Application No. 19180483.0; filed Jun. 17, 2019; European Search Report dated Nov. 27, 2019 (8 pages).

(Continued)

*Primary Examiner* — Yung-Sheng M Tsui
(74) *Attorney, Agent, or Firm* — Barclay Damon LLP

(57) ABSTRACT

A tablet press comprises a gate that defines a first switching position that feeds tablets into a first tablet outlet and at least a second switching position that feeds tablets into at least one second tablet outlet. The table press further comprises a control apparatus and a drive apparatus. The drive apparatus is configured to be actuated by the control apparatus to move the gate from a home position defined as one of the first switching position and the at least a second switching position into a target position defined as a switching position that is not the home position. The gate is moved from the home switching position at a speed of movement toward the target position such that the speed of movement of the gate is reduced before the target position is reached.

11 Claims, 2 Drawing Sheets

(56) References Cited

FOREIGN PATENT DOCUMENTS

| | | |
|---|---|---|
| EP | 2368704 A2 | 9/2011 |
| JP | 62071107 A1 | 7/1987 |
| JP | 205112500 U | 3/2016 |
| JP | 2015145020 A | 2/2017 |
| WO | 2008/038070 A1 | 4/2008 |

OTHER PUBLICATIONS

Fette Compacting GMBH; Meissner et al; JP Application No. P2019-116855; Japanese Office Action dated Aug. 28, 2020 (5 pages).
Fette Compacting GMBH; Meissner et al; JP Application No. P2019-116855; English Translation of Japanese Office Action dated Aug. 28, 2020 (4 pages).
Fette Compacting GMBH: Meissner et al; Indian Application No. 201914022532; Indian Office Action dated Nov. 5, 2020 (8 pages).
Fette Compacting GMBH; Meissner et al; Chinese Application No. 201910589297.2; Chinese Office Action dated Dec. 14, 2020 (10 pages).
Fette Compacting GMBH; Meissner et al; Chinese Application No. 201910589297.2; English Translation of Chinese Office Action dated Dec. 14, 2020 (8 pages).

\* cited by examiner

GATE FOR A TABLET DISCHARGE OF A TABLET PRESS AND METHOD FOR ACTUATING A GATE

CROSS REFERENCE TO RELATED INVENTION

This application is based upon and claims priority to, under relevant sections of 35 U.S.C. § 119, German Patent Application No. 10 2018 116 143.34, filed Jul. 4, 2018, the entire contents of which are hereby incorporated by reference.

BACKGROUND

The invention relates to a gate for a tablet discharge of a tablet press, in particular a rotary tablet press, wherein a control apparatus is provided, and wherein a drive apparatus is provided that moves the gate between a first switching position in which tablets are fed to a first tablet outlet, and at least one second switching position in which tablets are fed to at least one second tablet outlet.

The invention moreover relates to a method for actuating a gate for a tablet discharge of a tablet press, in particular a rotary tablet press, in which the gate is moved between a first switching position in which tablets are fed to a first tablet outlet, and at least one second switching position in which tablets are fed to at least one second tablet outlet.

Rotary tablet presses have a plurality of upper and lower punches which are always assigned in pairs to a cavity of a die plate of a rotor of the rotary tablet press. While the rotor is rotating, the cavities are filled with the filling material to be pressed. In at least one pressing apparatus, the upper and lower punches are pressed against each other in the cavities to press the filling material into tablets. After pressing, the tablets are generally ejected out of the cavities by the lower punch and, for example, supplied by a scraper to a tablet discharge. The removed tablets are for example fed to different tablet outlets by using measured values from sensors of the rotary tablet press, for example tablet outlets for good tablets, for bad tablets, or for tablets for a sampling. To guide the tablets into different tablet outlets, gates are regularly found in tablet discharges of rotary tablet presses. Such gates can for example have a gate flap that is pivotably movable between for example two switching positions which direct the tablets, depending on the switching position, to a first tablet outlet or a second tablet outlet.

It is known to detect when the respective end positions of the gate are reached by means of sensors. Generally two sensors are provided for detecting the respective end position for a gate with two switching positions. If the sensors recognize that an end position has not been reached, a corresponding error message is output.

Corresponding to the high production capacities of modern rotary tablet presses, a significant stream of tablets flows through the tablet discharge. In so doing, the tablets flow with only a slight distance between each other. When switching the gate, this can lead to a clamping of tablets between the gate, for example the free end of a gate flap, and an opposite wall of the tablet discharge. Correspondingly, the gate cannot reach its target switching position. This can in turn lead to a tablet jam in the tablet discharge, and to a shutoff of the rotary tablet press due to a gate malfunction. This significantly restricts the availability of the rotary tablet press, and the manual effort for an operator to eliminate the malfunction is high. To eliminate a tablet jam, it is accordingly necessary to open the housing of the rotary tablet press which leads to an elevated health risk, in particular when the pressing materials are toxic. Moreover, it is regularly necessary to remove components such as the gate drives, the column of air, covers, etc. to make the region of the tablet jam accessible. The jammed tablets must be removed as well as any fragments, and the tablet discharge must be cleaned. Moreover, it must be checked whether any bad tablets or fragments have unintentionally entered into good production. Then the removed components must be remounted, and the rotary tablet press must be restarted.

Proceeding from the explained state of the art, the object of the invention is to provide a gate and a method of the aforementioned type by means of which the availability of the rotary tablet press is maximized even with high production capacities, and the effort and health hazard for operators is minimized.

BRIEF SUMMARY OF THE INVENTION

For a gate of the aforementioned type, the invention achieves the object in that the control apparatus is designed to actuate the drive apparatus to move the gate out of a home switching position or home position into a target switching position or target position such that the gate is moved starting from the home switching position at a speed of movement toward the target switching position, wherein the speed of movement of the gate is reduced before the target switching position is reached.

For a method of the aforementioned type, the invention achieves the object in that the gate, to move out of a home switching position into a target switching position, is moved starting from the home position at a speed of movement toward the target switching position, wherein the speed of movement of the gate is reduced before the target switching position is reached.

The gate can be moved between a first switching position that for example can form a home switching position, and at least one second switching position that for example can form a target switching position. The first switching position and the at least one second switching position, or respectively the home switching position and the target switching position, are each end positions of the gate, or respectively a gate flap of the gate. In these end positions, a separation between the discharge channels of the gate and hence a guidance of the stream of tablets into the desired tablet outlet are ensured. In at least one end position, the gate, or respectively a gate flap, can for example lie against an inner wall of a discharge channel of the tablet discharge. In at least one end position, it can however also form part of a partition wall between different discharge channels of the tablet discharge.

A control apparatus is provided for the gate according to the invention that emits a switching signal to move the gate between a first switching position and at least one second switching position. The control apparatus can emit the switching signal for example due to measured values from sensors of the tablet press, or due to inputs to take a sampling. For example, sensors of the rotary tablet press can recognize impermissible deviations of parameters by produced tablets. These measured values can be applied to the control apparatus, and the control apparatus can correspondingly output a switching signal to move the gate into a switching position in which the corresponding tablets are fed to a tablet outlet for bad tablets. When there is a signal for taking a sampling, the control apparatus can also output a switching signal to move the gate into a switching position in which a given tablet quantity is fed to a tablet outlet for sampling, i.e., a spot check. The control apparatus can simultaneously be the control apparatus for controlling the operation of the rotary tablet press (machine control). It can however also be a control apparatus separate from such a machine control.

Moreover, a drive apparatus is provided that moves the gate depending on the switching signal received from the control apparatus into the desired switching position. The drive apparatus can for example comprise an electric motor which moves the gate between the first and the at least one second switching position, for example pivots a gate flap. Electromagnetic drives, for example, would however also be conceivable.

According to the invention, the gate, when moving from a home switching position to a target switching position, is initially moved at a given speed of movement toward the target switching position. For example when the gate, or respectively a gate flap can be pivoted between the home switching position and the target switching position, the speed of movement can correspondingly be a speed of rotation of the pivoting movement. The given speed of movement can be constant or also a speed profile. For example, the speed of movement of the gate, or respectively a gate flap, may be accelerated starting from the home switching position once or several times, for example be accelerated continuously. Before the gate reaches its target switching position, the speed of movement of the gate is reduced. The gate is then moved onward into its target switching position.

The invention is based on the concept that a clamping of tablets between the gate and for example an opposing wall of the tablet discharge can be prevented when the gate is decelerated in its movement before reaching its target switching position, and in particular before reaching a position in which a tablet can be clamped by the gate. Due to the reduction of the speed of movement, it is ensured that a tablet located in a region critical with regard to clamping by the gate has sufficient time to flow out before clamping by the gate can occur. If the gate is then moved onward up to its target switching position after the reduction of the speed of movement, this region of the tablet discharge swept by the gate is already free of tablets. A clamping of tablets when the gate is switched is thus avoided from the onset according to the invention. Since any clamping of tablets is eliminated according to the invention, a tablet jam in the tablet discharge with the explained negative consequences can be safely prevented. A gate malfunction which in practice is one of the most frequent reasons for the stoppage of a rotary tablet press is prevented such that subsequent problems like a tablet jam and the associated consequences do not occur.

Since a tablet jam is prevented, the reliability and availability of the rotary tablet press is increased. Operators are protected from toxic products and associated health risks by automatically preventing the gate malfunction. Manual effort to eliminate a gate malfunction is avoided. Furthermore, since a stoppage of the rotary tablet press and a subsequent starting process can be avoided, the arising waste is significantly reduced in comparison to the prior art. Moreover, increased tablet quality can be achieved by reduced mechanical stress on the tablets.

The gate can be moved onward up to the target switching position by the drive apparatus controlled by the control apparatus after the reduction of the speed of movement, for example at the constant reduced speed of movement. In order to reduce the switching time, it is however also possible after the speed reduction for the speed of movement of the gate to be further increased by the drive apparatus controlled by the control apparatus; the gate is therefore reaccelerated for example up to a given maximum speed. In addition for the movement of the gate after the speed reduction until the target switching position is reached, a speed profile can be traverse by means of the drive apparatus controlled by the control apparatus. For example, the speed of movement of the gate, or respectively a gate flap, may be accelerated once or several times after the speed reduction, for example accelerated continuously. In a manner known per se, at least one sensor that is known per se can be provided that detects at least one, preferably all end positions of the gate, i.e., the first and the at least one second switching position, or respectively the home switching position and the target switching position. In so doing, the end positions can be detected directly or indirectly. For example, the sensor or the sensors can also deduce from other measured values when the respective end position is reached or not reached. For example, induction sensors or microswitches are possible as sensors which recognize when each given end position is reached or not reached. Of course, they can also be different sensors. An angle sensor is also cited as an example that detects the angular position of the gate such as a gate flap, and accordingly can detect all the end positions and preferably also any intermediate positions of the gate. Such an angle sensor is particularly suitable when a given speed profile is to be traversed. The point in time of the gate speed reduction can also be established with such an angle sensor in a particularly easy manner. During a movement of the gate out of a home switching position such as the first switching position into a target switching position such as the at least one second switching position, the at least one sensor can detect whether or not the target switching position was reached. The measuring signals from the at least one sensor can be applied to the control apparatus.

According to one embodiment, the control apparatus can be designed to actuate the drive apparatus such that the speed of movement of the gate is reduced to zero before reaching the target switching position, and the gate is then moved onward into the target switching position. In this extreme case, there is therefore a reduction of the speed of movement up to a stoppage. The speed of movement is reduced such that the gate, for example a gate flap, in its stoppage position cannot yet clamp any tablet that may be located between the gate, or respectively gate flap and an opposing wall. In the stoppage position of the gate, or respectively the gate flap, the distance between the gate, or respectively the gate flap and for example an opposing wall is accordingly greater than the diameter of the (largest) tablet conveyed through the tablet discharge. For example, this distance can be at least 10 mm, preferably at least 19 mm, and more preferably at least 25 mm. After reaching the stoppage, the gate is moved (onward) to its target switching position. There is therefore sufficient time for any tablets located in intermediate region to flow out. In this context, a defined stoppage time can be specified, after the expiration of which the control apparatus actuates the drive apparatus to further move the gate into its target switching position. In so doing, there is preferably no reversal of the direction of movement of the gate.

The tablet discharge can have at least one discharge channel as is known per se. In particular, the tablet discharge can have several discharge channels between which the gate can deflect the stream of tablets. Each discharge channel can lead to one of the tablet outlets. As already explained, the tablet outlets can for example lead to an outlet for bad tablets, for good tablets, or to a measuring apparatus for a sampling.

The gate can comprise at least one gate element, preferably a gate flap pivotably mounted in the at least one discharge channel of the tablet discharge between the first switching position and the at least one second switching position. Such a gate flap is an elongated body which is preferably pivotably mounted in the region of its one end on the discharge channel. The opposite free end of the gate flap then executes the maximum pivoting movement. The free end of the gate flap can be arranged upstream from the pivot bearing viewed in the discharge direction of the tablets. The gate flap can for example consist of a metal material. This is known per se. Of course, the gate can also comprise several such gate flaps arranged sequentially in the direction of flow of the tablets in order for example to be able to switch between three discharge channels.

According to another embodiment, the control apparatus can be designed to actuate the drive apparatus such that the speed of movement is reduced when there is a distance of more than 10 mm, preferably more than 19 mm, more preferably more than 25 mm between the at least one gate element, preferably the gate flap, in particular the free end of the gate flap, and an inner wall of the at least one discharge channel bordering the target switching position. It is thereby very reliably ensured that tablets located in the switching region of the gate element can still flow out on time.

According to another embodiment, at least one discharge channel can have at least one section that expands in the discharge direction of the tablets, preferably that expands in steps. According to another embodiment, the at least one expanding section can be located upstream in the discharge direction of the tablets, preferably directly upstream, from the region swept by the gate flap, for example its free end, during its pivoting movement. It is moreover advantageous when at least one expanding section is provided that expands, preferably expands in steps, on opposing walls of the discharge channel. According to another embodiment, the expansion of the at least one expanding section or expanded portion can have a width of at least 10 mm, preferably at least 19 mm, and more preferably at least 25 mm. The width is measured in a direction perpendicular to the direction of flow of the tablets, or respectively the longitudinal axis of the discharge channel. In this case, the width is preferably at least as wide as the largest tablet to be conveyed through the discharge channel.

The aforementioned preferably stepwise expansion forms a switching bay. In particular, the width of the discharge channel increases here. The expansion can be located in the region of one or all target switching positions of the gate. The expansion is designed such that a tablet located therein does not hinder the remaining stream of tablets. A tablet jam is very reliably prevented.

According to another embodiment, the control apparatus can be designed to actuate the drive apparatus so that the speed of movement of the gate is reduced directly before reaching the expanding section, or after reaching the expanding section. The slowing of the gate can therefore occur basically only upon reaching the expanding section, or the gate can already be located in the expanding section at the time at which the slowing begins. To the extent that the speed of movement is reduced to zero, the stoppage can also occur directly before the expanding section is reached or after the expanding section is reached, i.e., if the gate, for example a gate flap, is already located within the expanding section. The aforementioned measures prevent the gate such as a gate flap from impairing the stream of tablets because of its slowing, or respectively its stoppage. Instead, the slowing, or respectively stoppage can occur in or at the explained switching bay so that the remaining tablets can easily flow by the gate, such as a gate flap. In particular, it can be provided that the gate such as a gate flap does not substantially project in its stoppage position (inwardly) beyond the guide section of the discharge channel located directly in front of the expanding section in the discharge direction of the tablets. This guide section can also be formed by a wall of the discharge channel or also by a gate, or respectively gate flap, located upstream in the discharge direction when there are several sequentially arranged gates or respectively gate flaps.

The invention also relates to a rotary tablet press comprising a rotor that can be rotated by means of a rotary drive, wherein the rotor has an upper punch guide for upper punches of the rotary tablet press, a lower punch guide for lower punches of the rotary tablet press and a die plate arranged between the punch guides, wherein the punches interact with cavities in the die plate, furthermore comprising a filling apparatus by means of which the filling material to be pressed is added to the cavities in the die plate, furthermore comprising at least one upper pressing apparatus and at least one lower pressing apparatus that, during operation, interact with the upper punches and the lower punches such that they press the filling material into tablets in the cavities in the die plate, moreover comprising an ejection apparatus in which the tablets generated in the cavities are ejected, and moreover comprising a tablet discharge that is fed the ejected tablets, wherein at least one gate according to the invention is arranged in the tablet discharge.

The method according to the invention can be performed with a gate according to the invention or a rotary tablet press according to the invention. Accordingly, the gate according to the invention or the rotary tablet press according to the invention can be designed to perform the method according to the invention.

BRIEF DESCRIPTION OF THE DRAWINGS

An exemplary embodiment of the invention is explained below in greater detail with reference to figures. Schematically.

The same reference numbers refer to the same objects in the figures unless indicated otherwise.

DETAILED DESCRIPTION OF THE INVENTION

Figure 1:
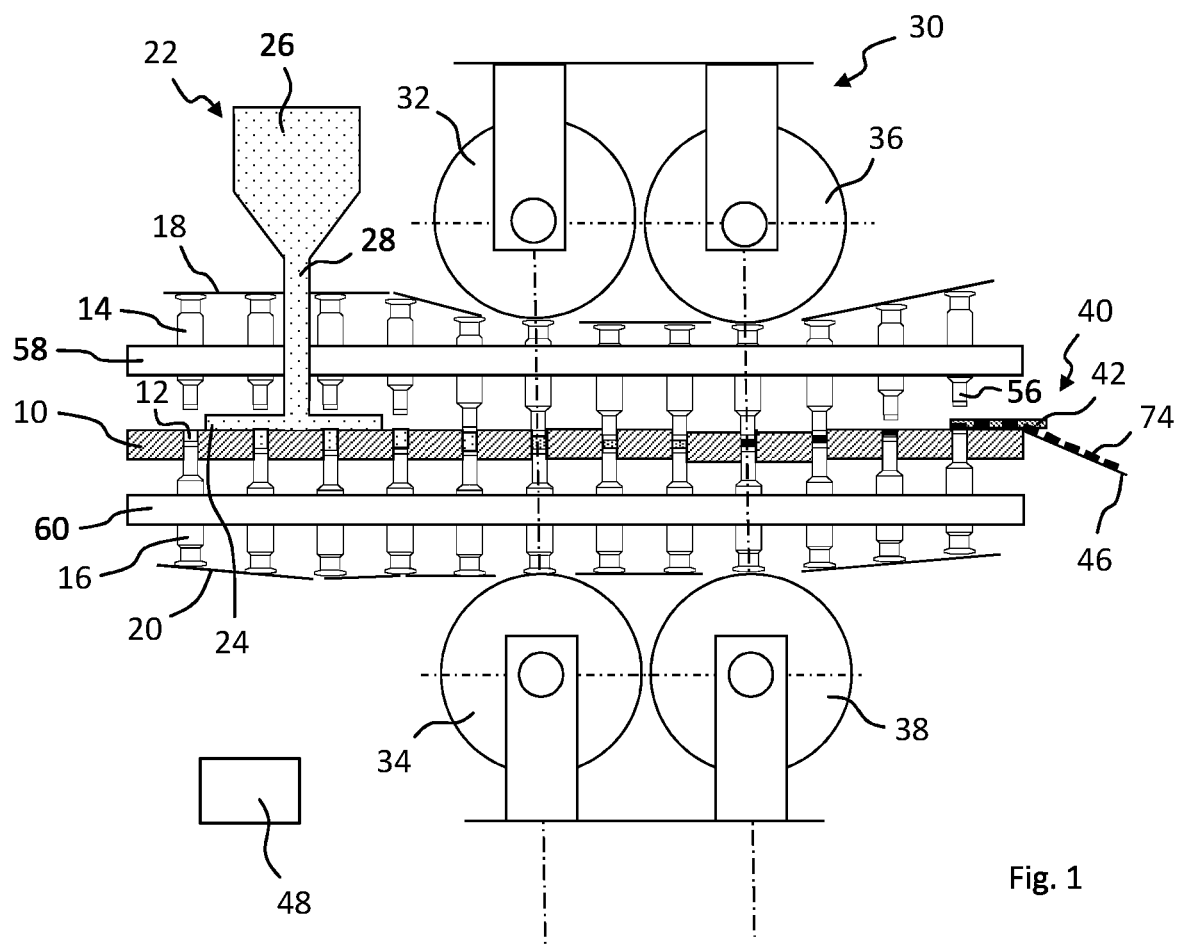
FIG. 1 illustrates a cross-sectional view of an embodiment of a rotary press.
Figure 2:
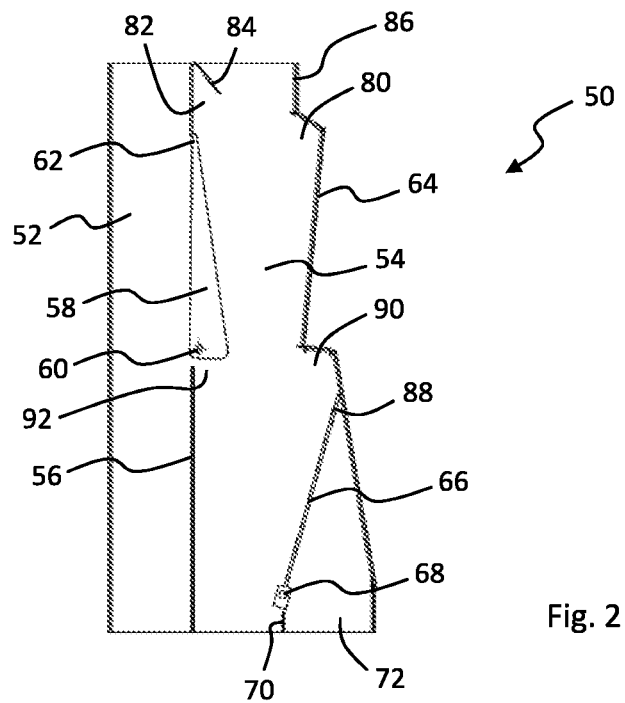
FIG. 2 illustrates a top plan view of an embodiment of a gate of the rotary tablet press shown in FIG. 1 in a first operating position.

The rotary tablet press shown in FIG. 1 comprises a rotor that is rotationally driven by a rotary drive (not shown) with a die plate 10 which has a plurality of cavities 12. The cavities 12 can for example be formed by holes in the die plate 10. Furthermore, the rotor comprises a plurality of upper punches 14 and lower punches 16 that rotate synchronously with the die plate 10. In each case, a pair consisting of an upper punch 14 and lower punch 16 is thus assigned to a cavity 12. The axial movement of the upper punches 14 and lower punches 16 during the rotation of the rotor is controlled by upper control cam elements 18 and lower control cam elements 20. The rotary tablet press moreover comprises a filling apparatus 22 which has a filling chamber 24. The filling apparatus 22 moreover comprises a funnel-shaped filling material reservoir 26 which is connected by a feed section 28 to the filling chamber 24. In this manner, the powdered filling material in the present example passes under the force of gravity from the filling material reservoir 26 via the feed section 28 into the filling chamber 24, and passes therefrom via a filling opening provided in the bottom side of the filling chamber 24 into the cavities 12 of the die plate 10, again under the force of gravity.

Moreover, the rotary tablet press comprises a pressing apparatus 30. The pressing apparatus 30 possesses a pre-pressing apparatus with an upper pre-pressing roller 32 and a lower pre-pressing roller 34, as well as a main pressing apparatus with an upper main pressing roller 36 and a lower main pressing roller 38. Furthermore, the rotary tablet press comprises an ejecting apparatus 40, in the present case with a scraper 42 which supplies the tablets 74 produced in the rotary tablet press to a tablet discharge 46.

A control apparatus for operating the rotary press is shown with reference number 48. The control apparatus 48 can for example comprise a computer processor, microprocessor, microcontroller, or similar device. The control apparatus 48 is connected by lines (not shown) to, inter alia, the rotary drive of the rotor.

A gate 50 shown in FIGS. 2 to 5 is located in the tablet discharge 46. The gate 50 has a first discharge channel 52 and a second discharge channel 54. The first and the second discharge channel 52, 54 are separated by a partition wall 56 from each other. A first gate flap 58 located in the partition wall 56 is mounted pivotably about a first pivot axis 60 between the first switching position shown in FIG. 2 and a second switching position (not shown) in which the free end 62 of the gate flap 58 lies against the opposite wall 64 of the second discharge channel 54. In FIGS. 2 to 5, tablets flow from top to bottom through the gate 50. Downstream from the first gate flap 58, a second gate flap 66 is pivotably mounted about a second pivot axis 68 in the second discharge channel 54 between a first switching position shown in FIG. 2 and a second switching position shown in FIG. 4. Downstream from the second gate flap 66, a partition wall 70 can be seen that defines a third discharge channel 72. Drives of a drive apparatus are provided such as electric motor or electromagnetic drives to pivot the first gate flap 58 and the second gate flap 66 between their respective first and second switching position. In addition, sensors (not shown) which are known per se can be provided that detect the reaching of the respective end positions of the gate flaps 58, 66, i.e., the respective first switching position and the respective second switching position. The detection signals of the sensors can also be applied to the control apparatus 48 in the shown example.

Figure 3:
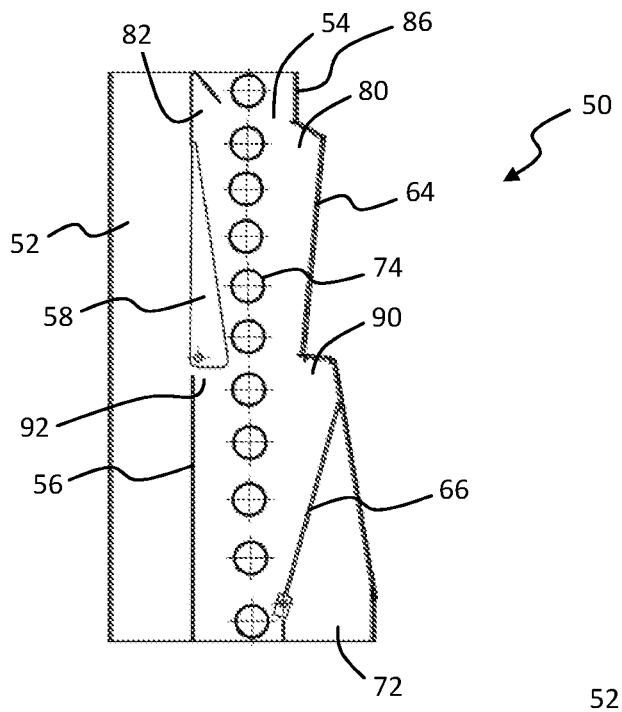
FIG. 3 illustrates a top plan view of the gate from FIG. 2 in a second operating position.
Figure 4:
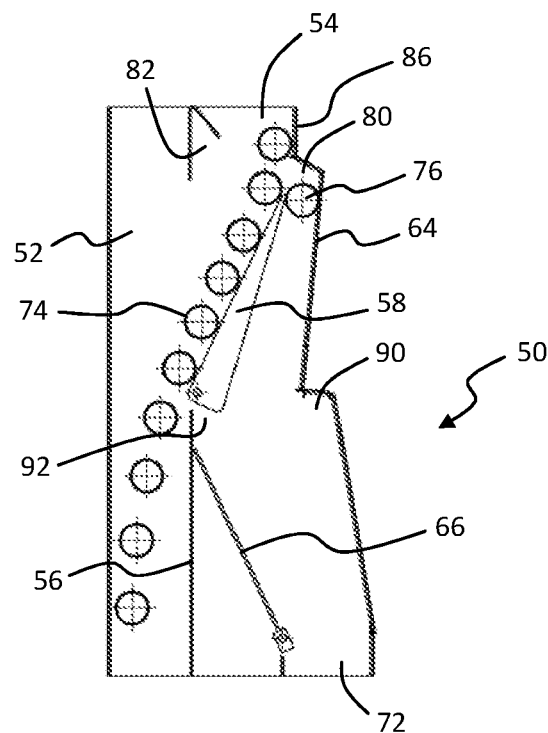
FIG. 4 illustrates a top plan view of the gate from FIG. 2 in a third operating position.
Figure 5:
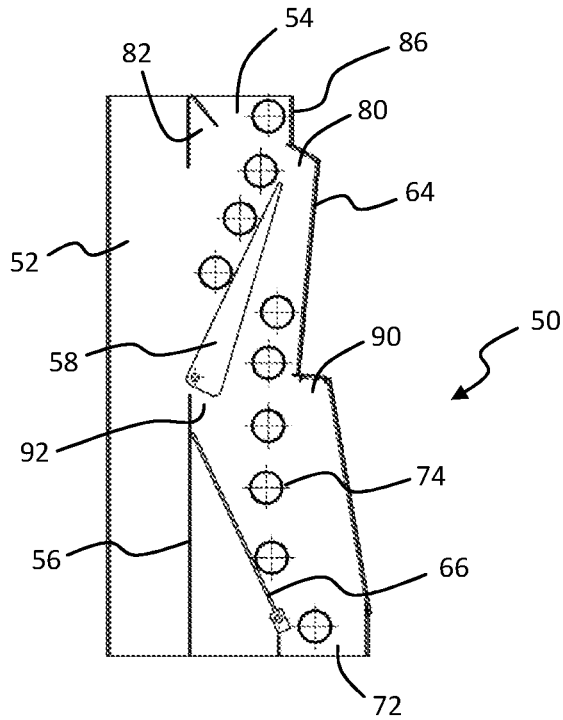
FIG. 5 illustrates a top plan view of the gate from FIG. 2 in a fourth operating position.

Tablets 74 which are discharged through the gate 50 for different operating states of the gate 50 are shown in FIGS. 3 to 5. As can be seen in FIG. 3, the tablets 74 traverse the second discharge channel 54 when the first gate flap 58 and the second gate flap 66 are in the first switching position. If contrastingly the first gate flap 58 moves toward its second switching position as shown in FIG. 4, the stream of tablets 74 is deflected from the second discharge channel 54 into the first discharge channel 52. Only when the first gate flap 58 is located in its first switching position does the stream of tablets 74 reach the second gate flap 66. Depending on its switching position, this deflects the stream of tablets 74 into the third discharge channel 72 (see FIG. 5) or closes the access to the third discharge channel 72 so that the stream of tablets 74 can continue to flow through the second discharge channel 54.

The second discharge channel 54 can for example lead to a tablet outlet for good tablets. The third discharge channel 72 can for example lead to a tablet outlet for a sampling. The first discharge channel 52 can for example lead to a tablet outlet for bad tablets.

In FIG. 4, a tablet 76 for example is shown clamped between the first gate flap 58 and the opposite wall 64. For this reason, the first gate flap 58 cannot reach its second switching position. The lack of reaching the second switching position can be detected by the respective sensor and output to the control apparatus. This then outputs a gate malfunction which can lead to a stoppage of the rotary tablet press.

To avoid this, it is provided according to the invention that the speed of movement of the first gate flap 58 and the second gate flap 66 is slowed before the target switching position is reached during an adjustment from a home switching position to a target switching position so that any tablet 76 located in a critical region for clamping can still flow out in a timely manner before clamping occurs. The respective gate flap 58, 66 can correspondingly safely reach its target switching position, and a gate malfunction is avoided.

It can for example be provided that the first gate flap 58 and/or the second gate flap 66 is braked up to the point of stopping before reaching its target switching position. This is shown for example in FIG. 5 for the first gate flap 58. The gate flap 58 was moved starting from its first switching position toward the second switching position, and braked in the stoppage position shown in FIG. 5 before reaching the second switching position. After reaching the stoppage position and possibly after the expiration of a given stoppage period, the gate flap 58 is adjusted further toward its second switching position. This can very reliably prevent a clamping of tablets.

It can also be seen in FIGS. 2 to 5 that the second discharge channel 54 expands in width on both sides directly upstream from the region swept by the first gate flap 58 during its pivoting movement, in particular the region swept by its free end 62. The expanding sections are shown with reference numbers 80 and 82. In this context, it is discernible that the expanding section 82 is formed because an upstream constriction from a wall projection 84 terminates. The sections 80, 82 that expand stepwise in the shown example each substantially correspond in the shown example to the width of the tablets 74, 76 to be diverted by the gate 50. As shown for example in FIG. 5 with regard to the first gate flap 58, said flap is brought to a stop directly upon reaching the expanding section 80. This ensures that the gate flap 58 brought to a stoppage does not impair the remaining stream of tablets 74. In particular, the free end 62 of the first gate flap 58 basically does not project inwardly beyond the wall section 86 located directly upstream from the expanded section 80. Apart from that, the function explained in this regard is otherwise equivalent for the first gate flap 58 and the opposing expanded section 82 as well as for the second gate flap 66. There is also a section 90, 92 with an expanded width in the second discharge channel 54 located on opposing sides directly upstream from the region swept by the free end 88 of the second gate flap 66 during its pivoting movement. The expanded section 92 is formed by the end of the first gate flap 58—the bottom end in FIG. 2—of the constriction of the second discharge channel 54. In the same manner as explained above with reference to the first gate flap 58, the expanded sections 90, 92 also enable a slowing, or respectively a stoppage of the second gate flap 66, for example upon reaching the respective expanded section 90, 92 so that the remaining stream of tablets 74 is not impaired. The expansion 90, 92 also substantially corresponds in its width to the diameter of the tablets 74, 76 to be diverted by the gate 50.

LIST OF REFERENCE NUMBERS

10 Die plate
12 Cavities
14 Upper punches
16 Lower punches
18 Upper control cam elements
20 Lower control cam elements
22 Filling apparatus
24 Filling chamber
26 Filling material reservoir
28 Feed section
30 Pressing apparatus
32 Upper pre-pressing roller
34 Lower pre-pressing roller
36 Upper main pressing roller
38 Lower main pressing roller
40 Ejection apparatus
42 Scraper
46 Tableting discharge
48 Control apparatus
50 Gate
52 First discharge channel
54 Second discharge channel
56 Partition wall
58 First gate flap
60 First pivot axis
62 Free end
64 Wall
66 Second gate flap
68 Second pivot axis
70 Partition wall
72 Third discharge channel
74 Tablets
76 Tablet
80 Expanded section
82 Expanded section
84 Wall projection
86 Wall section
88 Free end
90 Expanded section
92 Expanded section

The invention claimed is:

1. A tablet press comprising:
a gate of a tablet discharge defining a first switching position that feeds tablets into a first tablet outlet and at least a second switching position that feeds tablets into at least one second tablet outlet;
at least one discharge channel comprising at least one section that expands along a tablet discharge direction, wherein the at least one section that expands is formed from a termination of an upstream constriction from a wall;
a control apparatus configured to emit a switching signal; and
a drive apparatus configured to receive the switching signal, wherein the drive apparatus is configured to actuate in response to the switching signal to move the gate from a home position defined as one of the first switching position and the at least a second switching position into a target position defined as a switching position that is not the home position,
wherein the control apparatus is configured to control the drive apparatus via the switching signal such that the gate is moved from the home switching position at a speed of movement toward the target position and, wherein the speed of movement of the gate is reduced before the target position is reached, and
wherein the control apparatus is configured to control the drive apparatus via the switching signal to accelerate the speed of movement of the gate one or more times after the speed of movement of the gate is reduced.

2. The tablet press according to claim 1, wherein the control apparatus is configured to actuate the drive apparatus to reduce the speed of movement of the gate to stop the gate before reaching the target position, and wherein the speed of movement of the gate is then increased to move the gate into the target position.

3. The table press according to claim 1, wherein the gate comprises at least one gate element pivotably mounted within the at least one discharge channel of the tablet discharge between the home position and the target position.

4. The tablet press according to claim 3, wherein the control apparatus is configured to actuate the drive apparatus to reduce the speed of movement of the gate when there is a distance of more than 10 mm between the at least one gate element and an inner wall of the at least one discharge channel bordering the target position.

5. The tablet press according to claim 4, wherein the at least one expanding section is located upstream from a region swept by the gate element during its pivoting movement.

6. The tablet press according to claim 1, wherein at least one expanding section expands opposing walls of the discharge channel.

7. The tablet press according to claim 1, wherein the expansion of the at least one expanding section has a width of at least 10 mm.

8. The tablet press according to claim 2, wherein the control apparatus is configured to actuate the drive apparatus so that the speed of movement of the gate is reduced before reaching an expanding section or after reaching the expanding section.

9. The tablet press according to claim 1, further comprising a plurality of sensors configured to measure parameters of tablets entering the gate.

10. The tablet press according to claim 9, wherein the measured parameters are transmitted to the control apparatus, and wherein the switching signal is generated in response to impermissible deviations of the measured parameters.

11. A tablet press comprising:
a tablet discharge comprising at least one discharge channel;
a gate of a tablet discharge defining a first switching position that feeds tablets into a first tablet outlet and at least a second switching position that feeds tablets into at least one second tablet outlet;
a control apparatus configured to emit a switching signal;

a drive apparatus in communication with the control apparatus and configured to be actuated in response to the switching signal in order to move the gate from a home position defined as one of the first switching position and the at least a second switching position into a target position defined as a switching position that is not the home position; and at least one gate element pivotably mounted within the at least one discharge channel of the tablet discharge between the home position and the target position, wherein the at least one gate element is configured to pivot relative to the at least one discharge channel to sweep a region of the discharge channel, wherein the at least one discharge channel has at least one section that expands in width along a tablet discharge direction and is positioned upstream from at least one region that is swept, wherein the at least one section that expands is formed from a termination of an upstream constriction from a wall, wherein the gate is moved from the home switching position at a speed of movement toward the target position and, wherein the speed of movement of the gate is reduced before the target position is reached.

* * * * *